United States Patent [19]

Grollier et al.

[11] Patent Number: 4,851,154
[45] Date of Patent: Jul. 25, 1989

[54] DETERGENT AND FOAMING COSMETIC COMPOSITION DELAYING THE REGREASING OF HAIR

[75] Inventors: Jean F. Grollier; Chantal Fourcadier; Monique Courtois, all of Paris, France

[73] Assignee: L'Oreal, Paris, France

[21] Appl. No.: 178,508

[22] Filed: Apr. 7, 1988

[30] Foreign Application Priority Data

Apr. 10, 1987 [LU] Luxembourg .................. 86839

[51] Int. Cl.⁴ .................... C11D 1/9; C11D 1/94
[52] U.S. Cl. ............................ 252/546; 252/90; 252/545; 252/550; 252/551; 252/552; 252/555; 252/DIG. 13; 252/DIG. 14; 424/70
[58] Field of Search ............ 252/546, 547, 550, 551, 252/555, DIG. 13, DIG. 14, DIG. 5

[56] References Cited

U.S. PATENT DOCUMENTS

| | | | |
|---|---|---|---|
| 4,140,657 | 2/1979 | Okumura et al. | 252/551 |
| 4,554,098 | 11/1985 | Klisch et al. | 252/547 |
| 4,732,692 | 3/1988 | Zabotto et al. | 252/106 |
| 4,772,424 | 9/1988 | Greeb | 252/546 |

FOREIGN PATENT DOCUMENTS

| | | | |
|---|---|---|---|
| 168796 | 9/1985 | Japan | 252/546 |
| 2170216 | 7/1986 | United Kingdom . | |

*Primary Examiner*—Prince E. Willis
*Attorney, Agent, or Firm*—Marshall, O'Toole, Gerstein, Murray & Bicknell

[57] ABSTRACT

Detergent and foaming composition, delaying the regreasing of hair, containing a mixture of surface-active agents comprising:

an alkali metal, magnesium, ammonium or amine alkyl sulphate;

an alkali metal salt of an α-olefin sulphonate;

an alkali metal salt of an ethoxylated alkyl ether sulphate;

a compound corresponding to the formulae:

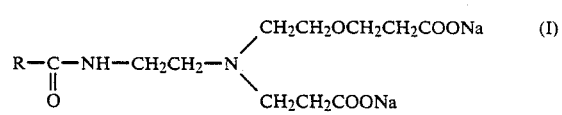

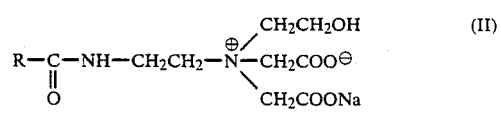

in which

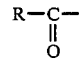

denotes an acyl radical derived from copra.

8 Claims, No Drawings

DETERGENT AND FOAMING COSMETIC COMPOSITION DELAYING THE REGREASING OF HAIR

The present invention relates to detergent and foaming compositions. These compositions are intended particularly to be employed as foaming shampoo delaying the regreasing of hair.

In many individuals, hair tends to have a greasy and unattractive appearance at the end of a few days which follow the washing, owing essentially to an exaggerated secretion of sebum by the sebaceous glands of the scalp.

To eliminate the unattractive greasy appearance of hair, it has already been proposed to incorporate sulphur-containing derivatives in cosmetic compositions such as shampoos or lotions.

The shampoos previously recommended for delaying the regreasing of hair present the disadvantage, however, of producing a foam which has a rough feel and is generally not very abundant.

It is known, in fact, that the sebum present on the hair tends to have a detrimental effect on the volume and the compactness of the foam which may be formed when the hair is washed. This generally leads the users to apply the detergent composition to the hair several times during the same single washing.

Applicants have found, and this forms the subject of the invention, that by combining a number of individual surfactants which are known per se, it was possible to obtain a shampoo permitting the emergence of the greasy appearance of the hair to be delayed efficiently while giving rise to the formation of a foam having the desired volume and compactness characteristics.

Applicants have found, in particular, that this combination of surface-active agents gave rise to an effect of synergism between the various constituents, which is demonstrated particularly by the characteristics of the foam formed.

One of the subjects of the invention consists, therefore, of a detergent and foaming composition delaying especially the regreasing of the hair.

Another subject of the invention is a process for washing the skin and/or the hair making use of a composition of this kind.

Other subjects of the invention will become apparent from reading the description and the examples which follow.

The detergent and foaming composition according to the invention is essentially characterized by the fact that it contains, in a cosmetically acceptable aqueous medium, a mixture of surface-active agents in proportions which are preferably between 8 and 15% by weight, comprising:

(i) an alkali metal, magnesium, ammonium or amine alkyl sulphate, in which the alkyl radical consists of a linear chain containing 12 to 18 carbon atoms, preferably employed in proportions of 1 to 4.5% by weight;

(ii) an alkali metal salt of an α-olefin sulphonate containing linear chains containing 12 to 18 carbon atoms, preferably employed in proportions of 1 to 5% by weight;

(iii) an alkali metal salt of an ethoxylated alkyl ether sulphate containing linear chains containing 12 to 18 carbon atoms, preferably employed in proportions of 0.5 to 5% by weight;

(iv) a compound corresponding to the formula:

$$R-\underset{\underset{O}{\|}}{C}-NH-CH_2CH_2-N\begin{matrix}CH_2CH_2OCH_2CH_2COONa\\ \\ CH_2CH_2COONa\end{matrix}$$

in which $$R-\underset{\underset{O}{\|}}{C}-$$

denotes the acyl radical derived from copra, or the compound corresponding to the formula:

$$R-\underset{\underset{O}{\|}}{C}-NH-CH_2CH_2\overset{\oplus}{N}\begin{matrix}CH_2CH_2OH\\ -CH_2COO^{\ominus}\\ CH_2COONa\end{matrix}$$

in which $$R-\underset{\underset{O}{\|}}{C}-$$

denotes the acyl radical derived from copra, preferably employed in proportions of 1 to 4% by weight.

In accordance with the invention, ammonium lauryl sulphate is preferably used as alkyl sulphate, sodium $C_{14}$–$C_{16}$ α-olefin sulphonate as α-olefin sulphonate, sodium lauryl ether sulphate oxyethylenated with 2.2 moles of ethylene oxide as alkali metal salt of ethoxylated alkyl ether sulphate and, as a compound of formula (I), the compound sold under the name Miranol C2M SF by the Miranol company and denoted in the CTFA dictionary, 3rd edition, 1982, by the name "Cocoamphocarboxypropionate".

As a compound of formula (II), use is made more particularly of the compound sold under the name Miranol C2M conc, sold by the Miranol company and appearing in the CTFA dictionary, 3rd edition, 1982, under the name cocoamphocarboxyglycinate.

The proportions indicated are proportions given relative to the total weight of the composition, the quantity of surface-active agents being between 8 and 15% relative to the total weight of the composition.

In addition to the various surface-active agents defined above, the compositions according to the invention may contain other adjuvants which are usually employed in cosmetics and particularly in washing compositions such as shampoos. To this end, there may be mentioned perfumes, preserving agents, sequestering agents, thickeners, softeners, foam stabilizers, and acidifying or alkalifying agents.

The thickeners may be chosen particularly from sodium alginate, gum arabic, cellulose derivatives such as methyl cellulose, hydroxymethyl cellulose, hydroxyethyl cellulose, hydroxypropyl cellulose, hydroxypropyl methyl cellulose, guar gum or its derivatives, xanthan gums and scleroglucans.

The thickening may also be obtained by mixing polyethylene glycol and stearates or polyethylene glycol distearates or by a mixture of phosphoric esters and amides.

These thickeners are preferably employed in proportions of 0.05 to 15% by weight relative to the weight of the composition.

In addition to water, the aqueous medium may contain cosmetically acceptable solvents such as monoalcohols, polyalcohols, glycol ethers, and fatty acid esters, employed by themselves or mixed. Among these solvents, more particular mention may be made of the lower alcohols such as ethanol, isopropanol, polyalcohols such as ethylene glycol, diethylene glycol, propylene glycol, glycol ethers, and glycol or diethylene glycol alkyl ethers.

The solvents are preferably employed in proportions of 0.5 to 10% by weight relative to the total weight of the composition.

The compositions may take various forms such as lotions, optionally thickened lotions, creams, gels or aerosol foams and may, for this purpose, contain known ingredients of the prior art for this type of application.

The compositions according to the invention may be employed for washing the skin or hair and more particularly as shampoos for hair, especially for greasy hair.

In this case, the composition is applied to wet hair, massage and rinsing are carried out and, if desired, the shampoo is applied once again, followed by further rinsing with water.

The following examples are intended to illustrate the invention without, however, being limiting in character.

EXAMPLE 1

A foaming, antigrease shampoo is prepared, corresponding to the following composition:

| | |
|---|---|
| ammonium lauryl sulphate | 4 g AS |
| sodium $C_{14}$-$C_{16}$ α-olefin sulphonate | 3 g AS |
| product known as cocoamphocarboxyglycinate sold under the name of Miranol C2M conc. by the Miranol company | 2 g AS |
| sodium lauryl ether sulphate oxyethylenated with 2.2 moles of ethylene oxide | 1 g AS |
| HCl | q.s. pH 6 |
| perfume | q.s. |
| water | q.s. 100 g |

This composition is applied to greasy and wet hair and massaged in; the formation of a foam exhibiting good volume and good compactness is observed.

After rinsing, the hair is dried. It is found that it is nongreasy in appearance and that it tends to regrease more slowly than the known shampoos of the state of the art.

EXAMPLE 2

A transparent gel for the skin and hair is prepared, corresponding to the following composition:

| | |
|---|---|
| ammonium lauryl sulphate | 4.5 g AS |
| sodium $C_{14}$-$C_{16}$ α-olefin sulphonate | 4 g AS |
| product known as cocoamphocarboxyglycinate sold under the name of Miranol C2M conc. by the Miranol company | 2.5 g AS |
| sodium lauryl ether sulphate oxyethylenated with 2.2 moles of ethylene oxide | 4. g AS |
| HCl | q.s. pH 6 |
| perfume | q.s. |
| water | q.s. 100 g |

EXAMPLE 3

A shampoo of the following composition is prepared:

| | |
|---|---|
| ammonium lauryl sulphate | 1 g AS |
| sodium $C_{14}$-$C_{16}$ α-olefin sulphonate | 5 g AS |
| product known as cocoamphocarboxyglycinate sold under the name of Miranol C2M conc. by the Miranol company | 1 g AS |
| sodium lauryl ether sulphate oxyethylenated with 2.2 moles of ethylene oxide | 3 g AS |
| hydroxyethyl cellulose sold by the Hercules company under the name Natrosol 250 HHR | 0.5 g |
| HCl | q.s. pH 5 |
| perfume | q s. |
| water | q.s. 100 g |

EXAMPLE 4

A shampoo of the following composition is prepared:

| | |
|---|---|
| ammonium lauryl sulphate | 3 g AS |
| sodium $C_{14}$-$C_{16}$ α-olefin sulphonate | 1 g AS |
| product known as cocoamphocarboxyglycinate sold under the name of Miranol C2M conc. by the Miranol company | 3 g AS |
| sodium lauryl ether sulphate oxyethylenated with 2.2 moles of ethylene oxide | 5 g AS |
| NaCl | 1 g |
| triethanolamine | q.s. pH 8.2 |
| perfume | q.s. |
| water | q.s. 100 g |

We claim:

1. A detergent and foaming composition delaying the regreasing of hair, containing, in a cosmetically acceptable aqueous medium, a mixture of surface-active agents, comprising:
   - 1–4.5% by weight, based on said composition, of an alkali metal, magnesium, ammonium or amine alkyl sulphate in which the alkyl radical has a linear chain containing 12 to 18 carbon atoms;
   - 1–5% by weight, based on said composition, of an alkali metal salt of an α-olefin sulphonate containing linear chains containing 12 to 18 carbon atoms;
   - 0.5–5% by weight, based on said composition, of an alkali metal salt of an ethoxylated alkyl ether sulphate containing linear chains containing 12 to 18 carbon atoms;
   - 1–4% by weight, based on said composition, of a compound corresponding to the formulae:

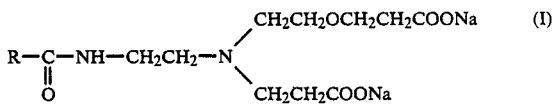

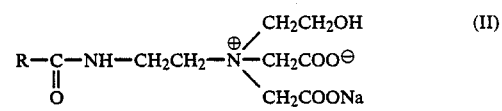

in which

denotes an acyl radical derived from copra.

2. A composition according to claim 1, wherein the mixture of surface-active agents is present in proportions of 8 to 15% by weight relative to the total weight of the composition.

3. A composition according to claim 1, which contains ammonium lauryl sulphate, a sodium $C_{14}$-$C_{16}$ α-olefin sulphonate, sodium lauryl ether sulphate oxyethylenated with 2.2 moles of ethylene oxide and cocoamphocarboxyglycinate corresponding to the formula (II) as defined in claim 1.

4. A composition according to claim 1, which is in in the form of a lotion, thickened lotion, cream, gel or aerosol foam.

5. A composition according to claim 1, wherein the cosmetically acceptable aqueous medium contains, in addition to water, a solvent chosen from monoalcohols, polyalcohols and glycol ethers, employed by themselves or mixed.

6. A composition according to claim 1, which contains various adjuvants usually employed in cosmetics selected from perfumes, preserving agents, sequestering agents, thickeners, softeners, foam stabilizers, and acidifying or alkalifying agents.

7. Process for washing hair, or the skin, consisting in applying to the wet skin or hair at least one composition such as defined in claim 1.

8. Process for washing hair, wherein at least one composition such as defined in claim 1 is applied to the hair and that rinsing is then carried out, optionally followed by a new application, followed by a new rinse.

* * * * *